United States Patent [19]

Chase

[11] Patent Number: 4,480,465

[45] Date of Patent: Nov. 6, 1984

[54] DEVICE FOR DEPENDENTLY SUPPORTING POTTED PLANTS HAVING VISUAL MOISTURE-INDICATING MEANS

[76] Inventor: John G. Chase, 1602 E. Dorchester Dr., Palm Harbor, Fla. 33563

[21] Appl. No.: 518,004

[22] Filed: Jul. 28, 1983

[51] Int. Cl.³ .......................... A01G 9/02; G01D 11/00
[52] U.S. Cl. ............................................. 73/73; 47/67;
116/200; 116/215; 116/DIG. 32
[58] Field of Search ............... 116/109, 215, 212, 227,
116/229, 297, DIG. 32, 200; 73/73, 296, 337;
47/39, 67; 177/232–234, 225, 229

[56] References Cited

U.S. PATENT DOCUMENTS

| | | | |
|---|---|---|---|
| 1,190,632 | 7/1916 | Collette | 177/229 |
| 2,586,245 | 2/1952 | McRae | 177/232 |
| 2,861,790 | 11/1958 | Stevens | 177/229 |
| 3,191,702 | 6/1965 | Kohlhagen | 177/229 |
| 4,078,625 | 3/1978 | Loeb | 177/233 |
| 4,216,619 | 8/1980 | Espy | 47/67 |
| 4,256,195 | 3/1981 | Bovet | 177/232 |

Primary Examiner—Charles Frankfort
Assistant Examiner—Willie Morris Worth
Attorney, Agent, or Firm—Cushman, Darby & Cushman

[57] ABSTRACT

A device for visually indicating the moisture content of a potted plant includes a housing defining opposing openings in which an elongated flexible visual moisture indicating member is disposed. A reciprocally moveable support member is operatively associated with the housing and is fixed to the indicating member so that movement of the support member between high and low positions responsively effects flexible downward and upward displacement, respectively, of the exposed portion of the indicating member extending exteriorly of the housing. In such a manner, the moisture content of a potted plant can be quickly ascertained by visual inspection of the relative positioning of the exposed indicator member portion.

19 Claims, 2 Drawing Figures

U.S. Patent   Nov. 6, 1984   4,480,465
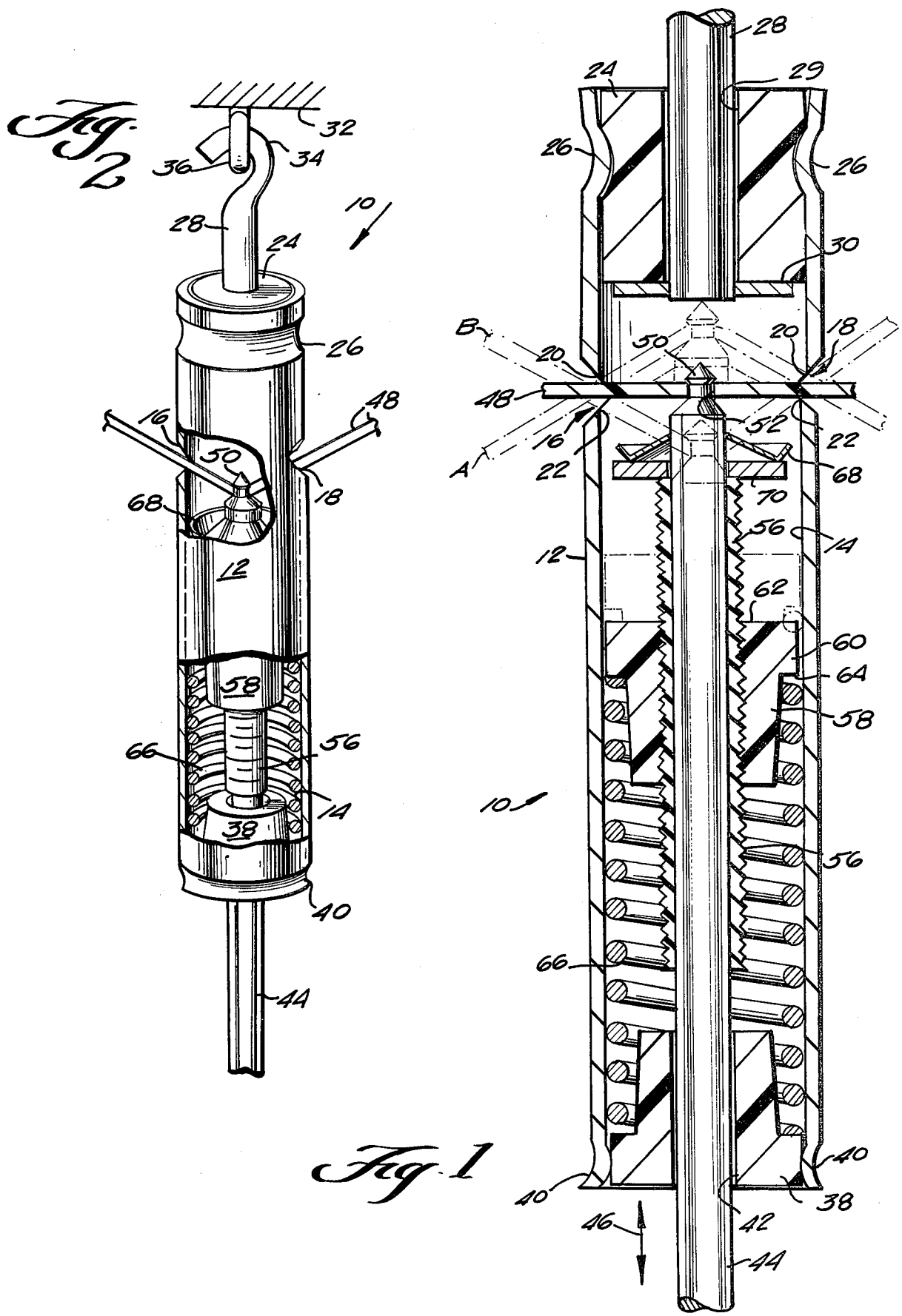

DEVICE FOR DEPENDENTLY SUPPORTING POTTED PLANTS HAVING VISUAL MOISTURE-INDICATING MEANS

BACKGROUND AND SUMMARY OF THE INVENTION

The present invention generally relates to a device for dependently supporting potted plants and particularly includes means for indicating the moisture content of the potted plants dependently supported thereby. In accordance with the present invention, one need only glance at the device so as to quickly ascertain whether the potted plant is in need of watering thereby obviating any special equipment for determining the moisture content of the potted plant and, particularly, the soil in which the potted plant is located.

Various attempts have been previously made for an implement which will dependently support a potted plant and, moreover, will provide some form of visual indication of the moisture content of the dependently supported potted plant. For example, U.S. Pat. No. 4,078,625 to Loeb discloses a hanging plant device having a body member in which a lower hook is slideably reciprocally moveable. A spring is provided in operative association with the lower hook so as to provide the necessary biasing tension thereagainst. Additionally, a threaded adjustment member is provided in accordance with the Loeb device so as to "zero" the visual indication means. According to Loeb, the visual indication of the moisture content in the soil of the plant's container is achieved by providing integral members 20 which are slideably received in slots in the device body. The members 20 are therefore capable of registering with indicia on the exterior of the body to indicate the moisture content in the soil of the plant's container. Thus, as the moisture content becomes greater, the hook member will be downwardly displaced thereby responsively slideably moving the indicating members 20 downwardly and registering them beside the appropriate moisture-indicating indicia. Of course, upon the moisture content of the plant becoming less, the reverse slideable operation of indicating members 20 will be effected.

U.S. Pat. No. 4,227,343 to Espy et al and U.S. Pat. No. 4,216,619 to Espy each disclose a hanging plant device having a linear to rotary motion converter in the form of spiral 40a. In Espy et al '343, the spiral 40a is axially integral with rod 12 which includes projection 13 which serves as an indicator when the plant is in a dry condition. Espy '619 is similar to Espy et al '343 in that a linear to rotary motion converter in the form of a spiral 21 is provided. A pointer 32 is operatively associated with spiral 21 so as to be registrable with indicia or moisture-indicating graduations 30 on slot 31 in which pointer 32 is slideably moveable in response to vertical linear displacement of shaft 21.

U.S. Pat. No. 3,967,579 to Gallow discloses a moisture gauge for hanging a potted plant which generally comprises a U-shaped spring element including a spring coil and a pair of approximately parallel arms extending from the spring coil and shaped to provide notches opposite one another at spaced intervals therealong. One of the arms terminates in an indicator while the other arm includes a cross-wise extension providing a moisture-indicating scale. In accordance with Gallow, a potted plant is dependently supported on one of the lower notches of the lower arm while its opposite corresponding notch of the upper arm is fixedly attached to a support member. Accordingly, the notches serve to extend the indicator as accurately as possible to the fully watered position.

U.S. Pat. No. 1,190,632 to Collette discloses a device for indicating the amount of water in a pail. The pail is dependently supported on the upper arm of a generally U-shaped spring member, the terminal end of which is connected to a pivotal indicator. Accordingly, the upper arm of the U-shaped spring member responsively effects transverse pivotal movement of the indicator so as to provide an indication of the liquid level in the pail.

As will become apparent from the discussion which follows, the present invention provides a novel advance over prior attempts at providing visual moisture-indicating means for dependently supporting potted plants. In accordance with the present invention, there is provided an aesthetically pleasing device which dependently supports potted plants, for example, and moreover, lends itself to quick viewing so as to ascertain the moisture content of the potted plant.

One of the problems associated with the above-identified prior hanging plant device proposals is that they operate upon the principle of viewing moisture-indicating indicia with which is registered a moveable element. In accordance with the present invention, however, opposing arms of a flexible indicator will either be displaced in an upward "V" fashion so as to indicate that the plant contains sufficient moisture or will be displaced in an "inverted V" fashion which will indicate that the potted plant is in a dry condition or is in need of moisture. Thus, the indicator member in accordance with the present invention will visually resemble the qualities of vegetation when they have sufficient moisture. That is, the vegetation will either be upwardly turned when sufficient moisture is present or will be wilted or downwardly turned when moisture is absent.

The present invention generally includes a body member in which is housed a slideable and reciprocally moveable plant supporting member. The body is fixedly supported to a rigid support member (such as the ceiling, hanging plant bracket or the like) while the plant support member dependently supports the potted plant thereon. The plant support member is reciprocally moveable relative to the housing and is attached to the visual indicator at the upper end thereof. The body defines opposing openings, each of which includes upper and lower bearing edges, the purpose of which will be described in more detail below. The visual indicator in accordance with the present invention is preferably constructed of a flexible, shape-retaining material such as plastic, light gauge metal or the like.

The plant support member is biased in an upward direction by suitable means such as, a compression spring, or the like. Thus, when the potted plant contains sufficient moisture, the added weight of such moisture will cause the plant support member to be downwardly displaced (e.g. so that the compression spring is at least partially compressed) and thus responsively deflect the visual indicator so that a portion thereof bears against the lower bearing edges of each of the opposed openings in the body housing. This functioning will deflect or displace the ends of the visual indicator which extend beyond the external periphery of the housing so as to effect a general V-shape of the visual indicator. Conversely, when the moisture content in the potted plant is depleted, the weight or force exerted upon the biasing spring will become less and thus the force of the spring will cause the plant support member to be upwardly displaced thereby bringing a portion of the visual indicator into bearing relationship with the upper bearing edges of the opposed openings in the housing thereby responsively deflecting the ends of the visual indicator extending beyond the external periphery of the housing into an "inverted V" position.

Means are also provided in accordance with the present invention so as to "zero" the visual indicator so as to provide a normal or benchmark moisture indication for any plant associated therewith and, moreover, to compensate for the additional weight caused by growth which the potted plant will hopefully experience.

These and other objects and advantages of the present invention will become more clear to the reader after careful consideration is given to the detailed disclosure thereof which follows.

BRIEF DESCRIPTION OF THE ACCOMPANYING DRAWINGS

Reference will be hereinafter made to the accompanying drawings which depict a particularly preferred embodiment of the present invention and wherein:

FIG. 1 is an elevational cross-sectional view of the device in accordance with the present invention; and FIG. 2 is a perspective view, partially in section, of the device in accordance with the present invention.

DETAILED DESCRIPTION OF THE PREFERRED EXEMPLARY EMBODIMENT

A preferred exemplary embodiment in accordance with the present invention is depicted in accompanying FIGS. 1 and 2 and the reader's attention is specifically directed thereto for the discussion which follows.

As shown therein, the device 10 generally includes a housing 12 defining an interior cavity 14. Opposing openings 16, 18 are provided in the housing 12 in the upper portion thereof, each of the openings 16, 18 defining upper and lower bearing edges 20, 22, respectively. Housing 12 is preferably constructed of a lightweight metal, such as, aluminum or the like, although rigid plastic material could also be utilized if desired.

The upper end of cavity 14 is closed by means of an upper plug member 24 which is frictionally fixed to housing 12 by means of crimped area 26. Support member 28 is loosely disposed in aperture 29 defined in upper plug member 24. Retaining washer 30 is rigidly fixed to support member 28 so that device 10 can be dependently supported from a rigid surface 32, such as the ceiling, hanging plant bracket or the like (see FIG. 2) but yet permit rotatable movement of housing 12 relative to support member 28. Preferably, the upper end of support member 28 is in the form of a hook 34 which cooperates with a similar hook or eye bolt 36, the latter being rigidly fixed to surface 32.

The lower end of housing 12 is closed by means of a lower plug member 38 which is fixed to housing 12 in a manner similar to upper plug member 24 e.g. by means of crimped area 40. Preferably, upper and lower plug members 24, 38 are constructed of a rigid plastic material although light-weight metal, such as aluminum, can also be advantageously employed. Lower plug member 38 defines an axially disposed aperture 42 in which plant support member 44 is received for sliding reciprocal movement therein (arrow 46 in FIG. 1).

The visual indication of the moisture content of the soil of a potted plant dependently supported by plant support member 44 is provided by flexible indicator 48 which is disposed in each opening 16, 18 and is of sufficient length so that a portion of indicator 48 extends beyond the external periphery of housing 12. Indicator 48 can be constructed of any suitable flexible yet shape-retaining material, such as plastic or the like and, additionally, can be of any desired cross-sectional configuration although a rectangularly-shaped cross section is presently preferred. Indicator 48 is fixed to the upper end of plant support member 44 by means of a retaining nib 50 cooperating with an aperture 52 defined in indicator 48.

Support member 44 is fixed to sleeve 56 which includes threads along the exterior thereof. Bushing 58 threadably cooperates with sleeve 56 and defines a flange portion 60 having upper and lower surfaces 62, 64, respectively. A compression spring 66 or other similar biasing means is fixed to and disposed between lower surface 64 of flange 60 and lower plug member 38. A tension spring could also be utilized if desired but would need to be positioned between upper plug 24 and bushing 64 to obtain the necessary and preferred upwardly biasing function.

Retaining pin 68 fixedly couples upper limit member 70 to sleeve 56. Thus, upper limit 70 acts as the upper limit of adjustment of bushing 60 whereas the lower edge of sleeve 56 operates as the lower limit of displacement of rod 44 relative housing 12.

The operation of device 10 in accordance with the present invention is as follows. A potted plant (not shown) is dependently supported from plant support member 44 and its weight operates against compression spring 66 so as to downwardly yieldably displace plant support member 44 and thus retaining nib 50 relative to housing 12. The downward displacement of nib 50 responsively causes a portion of visual indicator 48 to bear against lower edges 22 of opposing openings 16, 18. Thus, the flexible nature of indicator 48 will permit the ends thereof to be upwardly displaced as nib 50 is gradually downwardly displaced so that indicator 48 will eventually assume a general "V" position. Of course, once equilibrium is established, the indicator will maintain its "V" position until moisture is gradually depleted from the soil to reduce the weight of the potted plant. At such time, support member 44 will be gradually upwardly urged by the force of spring 66 thereby eventually bringing a portion of indicator 48 to bear against upper edges 20 of openings 16, 18 to flexibly displace the ends of indicator 48 into an "inverted V" position.

Preferably, the plant which is initially dependently supported from plant support member 44 is in a "dry" or moisture-lacking condition and, thus, the indicator 48 must be "zeroed" so as to compensate for the particular dry state of the plant in addition to its inherent weight. Such adjustment and compensation can be accomplished by turning support housing 12 relative to upper support member 28 and plant support member 44 so as to either upwardly or downwardly displace support member 44 (and sleeve 56) relative to bushing 60 by virtue of the threaded connection therebetween. That is, the force of spring 66 which is exerted upon bushing 60 can be adjusted so as to achieve the proper balance with respect to indicator 48 and the weight of the potted plant. Thus, when a plant in a "dry" condition is dependently supported from plant support member 44, member 44 should be turned relative to housing 12 so as to upwardly displace the central portion of indicator 48 and thus bring indicator 48 to bear against the upper edges 20 of opening 16, 18. The "dry" or "inverted V" position of indicator 48 is noted in phantom line in FIG. 1 as position A.

Once the indicator has been set in the above-described manner, water should be added to the potted plant so as to sustain its growth. The increased weight of the water added to the potted plant will cause a force to be exerted against the bias force of spring 66 so as to downwardly displace plant support member 44 and thus nib 50 relative to housing 12. The increased weight of the water being added to the potted plant will therefore responsively cause indicator 48 to be brought into bearing contact with lower edges 22 of openings 16, 18 and thus, continued added weight of water being supplied to the potted plant will cause the central portion of flexible indicator 48 to be downwardly displaced. Thus the lower edges 22 of openings 16, 18 will act as a fulcrum of sorts to upwardly displace the ends extending beyond the external periphery of housing 12. The "wet" or "V" position of indicator 48 is shown in FIG. 1 as position B.

Accordingly, as the moisture in the soil is consumed, evaporated or is otherwise removed therefrom, the weight of the plant will decrease to such an extent that the force exerted by spring 66 against bushing 58 will upwardly displace the plant support member (and the potted plant dependently supported thereby) so that when the potted plant is once again in the "dry" state, the indicator 48 will assume the position shown as A in phantom line in FIG. 1. Accordingly, one need only briefly glance at indicator 48 to determine whether the potted plant supported by device 10 in accordance with the present invention requires additional moisture so as to sustain its growth.

Of course, since the potted plant will grow and hopefully flourish thereby increasing its natural weight, it may be periodically necessary to compensate for this added weight by turning housing 12 relative to support members 28, 44 in the manner described above so as to once again "zero" indicator 48. Owing to the slow progression of growth in most potted plants, this periodic adjustment will, for all intents and purposes, be at significantly long spaced-apart intervals so that the moisture indication provided by indicator 48 will be reliable.

With suitable mechanical structures believed known to those in the art, the indicator 48 can be flexibly displaced in an opposite manner to that described above. Thus, indicator 48 can be displaced to an "inverted V" position to indicate high moisture content and to a "V" position to indicate a low moisture content, for example.

While the present invention has been herein described in what is presently conceived to be the most preferred and exemplary embodiment thereof, those in the art may realize that many modifications may be made hereof within the spirit and scope of the present invention, which scope is to be accorded the broadest interpretation of the appended claims so as to encompass all equivalent devices, assemblies and apparatus.

What is claimed is:

1. A device for visually indicating the moisture content of a potted plant comprising:
   a housing member defining a central cavity adapted to being dependently supported from a fixed object and including means defining a pair of substantially opposing openings, each said opening defining a pair of fulcrum surfaces;
   an elongated flexible member disposed in said pair of openings and having visual moisture indicating portions outwardly extending from each of said openings; and
   plant supporting means to support said potted plant and disposed in said central cavity, said plant supporting means including means permitting slideable reciprocal movement of said plant supporting means between first and second positions relative to said housing member in dependence upon the moisture content of said potted plant supported thereby, said plant supporting means being connected to said flexible member for flexibly displacing said visual moisture indicating portions in a first direction by bringing said flexible member into bearing contact with a predetermined one of said pair of fulcrum surfaces of each of said openings in response to said supporting means being displaced into said first position, and for flexibly displacing said visual moisture indicating portions in a second direction by bringing said flexible member into bearing contact with the other one of said pair of fulcrum surfaces of each of said openings in response to said supporting means being displaced into said second position wherein said visual moisture indicating portions in said first position visually indicate a high moisture content of said potted plant while said visual moisture indicating portions in said second position visually indicate a low moisture content of said plant.

2. A device as in claim 1 further comprising biasing means connected to said supporting means for biasing said supporting means into said second position.

3. A device as in claim 2 further comprising adjusting means operatively connected to said supporting means for adjustably moving said supporting means relative said housing between said first and second positions to responsively adjust the relative flexible displacement of said visual moisture indicating portions.

4. A device as in claim 3 wherein said supporting means includes means defining a threaded portion, said adjusting means including bushing means fixed to said biasing means and threadably connected to said supporting means for effecting vertical displacement of said supporting means in response to relative turning movement between said housing and said supporting means.

5. A device for visually indicating the moisture content of a potted plant comprising:
   a housing defining an interior cavity and including means defining at least one aperture including a pair of fulcrum surfaces;
   an elongated flexible moisture indicating member disposed in said at least one aperture and having one end positioned in said cavity and the other end positioned exteriorly of said housing: and
   support means positioned in said cavity and operatively connected to said one end of said moisture indicating member and being reciprocally moveable therein between first and second positions, said support means for dependently supporting said potted plant, said support means including means permitting reciprocal movement of said support means between said first and second positions in dependence upon the moisture content of said potted plant supported therefrom and for flexibly displacing said other end in a first direction by bringing a portion of said moisture indicating member into bearing contact with one of said pair of fulcrum surfaces in response to movement of said support means into said first position to indicate high moisture content of said potted plant and for flexibly displacing said other end by bringing a portion of said moisture indicating member into bearing contact with the other of said pair of fulcrum surfaces in response to movement of said support means into said second position to indicate low moisture content of said potted plant.

6. A device as in claim 5 further comprising biasing means connected to said support means for biasing said support means into said second position.

7. A device as in claim 6 further comprising adjusting means operatively connected to said support means for adjustably moving said support means relative said housing between said first and second positions to responsively adjust the relative flexible displacement of said other end of said moisture indicator member.

8. A device as in claim 5 further comprising adjusting means operatively connected to said support means for adjustably moving said support means relative said housing between said first and second positions to responsively adjust the relative flexible displacement of said other end of said moisture indicator member.

9. A device for dependently supporting and for visually indicating the weight of an object, said device comprising:
   elongated housing means defining an elongated central cavity and including means defining at least one aperture;
   supporting means slideably received in said cavity and including means to dependently support said object to effect reciprocal movement of said supporting means between first and second positions in dependence upon the weight of said object; and
   an elongated, axially flexible visual weight indicator means having one end connected to said supporting means and disposed in said at least one aperture so that a portion, which includes a second end of said weight indicator means outwardly extends from said aperture, for indicating the weight of said object at any predetermined time, said portion being axially flexed in a first direction to progressively upwardly displace said second end in response to movement of said supporting means towards said first position to indicate an increased weight of said object and being axially flexed in a second direction opposite to said first direction to progressively downwardly displace said second end in response to movement of said supporting means towards said second position to indicate a decrease in weight of said object.

10. A device as in claim 9 wherein said aperture defining means defines a pair of opposing apertures and wherein said weight indicator means is disposed in said pair of apertures so that portions outwardly extend therefrom, said supporting means being connected to substantially the middle of said indicator means.

11. A device as in claim 9 further comprising biasing means connected to said supporting means for biasing said supporting means into said second position.

12. A device as in claim 11 wherein said biasing means is a compression spring.

13. A device as in claim 11 further comprising adjusting means operatively connected to said supporting means for adjustably moving said supporting means relative said housing means between said first and second positions to responsively adjust the relative flexible displacement of said portion of said indicator means.

14. A device as in claim 13 wherein said supporting means includes a threaded portion and wherein said adjusting means includes bushing means threadably connected to said supporting means for effecting linear movement of said supporting means between said first and second positions in response to turning movement of said supporting means.

15. A device as in claim 9 further comprising adjusting means operatively connected to said supporting means for adjustably moving said supporting means relative said housing means between said first and second positions to responsively adjust the relative flexible displacement of said portion of said indicator means.

16. A device for dependently supporting a potted plant and for indicating the moisture content thereof comprising:
   housing means adapted to being dependently supported from a rigid member and defining an interior cavity, said housing means including means defining a pair of substantially opposing openings;
   plant supporting means having a portion received in said interior cavity and being reciprocally moveable between upper and lower positions for dependently supporting a potted plant at one end thereof;
   biasing means operatively connected to said plant supporting means for biasing said plant supporting means in an upward direction; and
   flexible indicator means for visually indicating the moisture content of said potted plant, said indicator means disposed in said pair of openings and having portions extending outwardly therefrom and connected to the other end of said plant supporting means, said portions being flexibly displaced between a first V-shaped position and a second inverted V-shaped position corresponding to high and low moisture contents of said potted plant in response to said plant supporting means being moved between said lower and upper positions, respectively.

17. A device as in claim 16 further comprising adjusting means operatively connected to said plant supporting means for adjustably moving said supporting means between said upper and lower positions to responsively adjust the relative flexible displacement of said portions between said first and second positions.

18. A device as in claim 17 wherein said adjusting means includes biasing means for biasing said supporting means into said upper position.

19. A device to visually indicate the weight of an object comprising:
   means for dependently attaching the object to a rigid surface and including (a) a housing member defining a pair of apertures, said housing member adapted to being fixed to said surface and (b) supporting means for supporting said object;
   said supporting means including mounting means for operatively interconnecting said supporting means and said housing member to permit said supporting means to be reciprocally movable, relative to said housing member, between first and second positions; and
   flexible indicator means attached to said supporting means and disposed in said pair of apertures so that portions thereof outwardly extend from said housing member; said indicator means for indicating the weight of the object by virtue of said portions thereof being flexed to a V-shaped position corresponding to a high weight of the object in response to said supporting means being moved to said first position and being flexed to an inverted V-shaped position in response to said supporting means being moved to said second position.

* * * * *